United States Patent
Yeung et al.

(12) 
(10) Patent No.: US 6,364,828 B1
(45) Date of Patent: Apr. 2, 2002

(54) ELONGATED FLEXIBLE INSPECTION NECK

(76) Inventors: Hubert K. Yeung, 251 S. Main St., Andover, MA (US) 01810; Roger A Dugas, 84 Great Oak Dr., Chester, NH (US) 03036

( * ) Notice: Subject to any disclaimer, the term of this patent is extended or adjusted under 35 U.S.C. 154(b) by 0 days.

(21) Appl. No.: 09/478,674

(22) Filed: Jan. 6, 2000

(51) Int. Cl.[7] ................................................ A61B 1/00
(52) U.S. Cl. ...................... 600/142; 600/134; 130/120; 174/68.3; 174/86
(58) Field of Search ...................... 600/134, 139–142; 604/95.04, 95.05; 138/120; 174/68.3, 86

(56) References Cited

U.S. PATENT DOCUMENTS

| | | | |
|---|---|---|---|
| 3,301,940 A | * | 1/1967 | Rischard et al. ............ 138/120 |
| 4,651,718 A | | 3/1987 | Collins et al. |
| 4,790,294 A | | 12/1988 | Allred, III et al. |
| 5,105,819 A | | 4/1992 | Wollschlager et al. |
| 5,178,129 A | | 1/1993 | Chikama et al. |
| 5,749,828 A | | 5/1998 | Solomon et al. |
| 5,807,241 A | * | 9/1998 | Heimberger ................ 600/142 |

FOREIGN PATENT DOCUMENTS

| | | |
|---|---|---|
| EP | 0626604 | 11/1994 |
| JP | 11-155806 | * 6/1999 |
| WO | WO 92/19147 | 11/1992 |

OTHER PUBLICATIONS

"Modern Machine Shop", Feb. 1999; pp. 68–71; vol. 71, No. 9.

* cited by examiner

*Primary Examiner*—John Mulcahy (57) ABSTRACT

An articulating elongated inspection neck effective to shield radio frequency interference. The inspection neck includes a series of individual electrically conducting parts each having a passageway there through. The parts are pivotally joined together with the passageways aligned along the length of the neck. A self-adjusting electrically conducting member connects immediately adjacent individual parts in electrical communication. The self-adjusting members maintain electrical communication between the parts throughout movement of the parts during flexure of the neck. Consequently, these members maintain electrical continuity along the length of the neck. The spacing between the parts is sized to be barrier to predetermined radio frequencies.

22 Claims, 11 Drawing Sheets

ELONGATED FLEXIBLE INSPECTION NECK

FIELD OF THE INVENTION

This invention relates to a flexible elongated neck and more particularly to an articulating elongated inspection neck effective to shield radio frequency interference.

BACKGROUND OF THE INVENTION

Invasive medical devices such as catheters, gastroscopes, colonscopes, endoscopes, and the like are commonplace in the diagnosis and the treatment of a variety of patient ailments. A medical professional inserts typically such devices into a patient and manipulates them to gather information about the patient's condition for review and analysis.

These medical devices usually include an elongated flexible neck incorporating a sensor or transducer at one end and positioning apparatus at the other end. The flexible neck facilitates insertion and remote manipulation via the positioning apparatus.

The sensor gathers relevant information on a patient under examination. Such information can include relatively simple information such as temperature. The information can include complex information such as imaging information. In these more complex situations electrical signals are transmitted via one or more signal wires, cables or fiber optics inside the elongated flexible neck. Signals transmitted during ultrasound imaging are an example of electrical signals transmitted inside the elongated flexible neck.

The operation environment of invasive medical devices is rich with troublesome radio frequency interference (RFI) and electromagnetic interference (EMI). For example, hospital intensive care units have patient monitoring electronics that tend to emit RFI. Also, the inductive nature of ventilators and other motor-based appliances also generate electronic noise. And in operating rooms, certain electro-surgical devices, such as self-cauterization apparatus, generates broadband electric noise.

The electrical signals transmitted in the elongated flexible neck are weak and of minimal amplitude. Consequently, the presence RFI and EMI can inhibit or confuse the signals of interest. Diagnosis and treatment are hindered.

Even medical devices using such reliable elongated articulating necks as disclosed in U.S. Pat. 5,749,828 do not shield against RFI. The patent discloses a bendable neck constructed using pivotally joined tubular sleeves. But the linkage does not guarantee electrical communication between the sleeves. Consequently, electrical continuity along the neck critical for RFI shielding can not be guaranteed.

The fact that there is no guaranteed electrical continuity between the tubular sleeves disclosed in U.S. Pat. No. 5,749,828 is the result of the inability of manufacturing techniques. These techniques can not fashion surfaces that keep electrical communication between the tubular sleeves during bending of the neck. Even with high precision machining techniques, the edge surfaces of the tubular sleeves can not guarantee electrical communication throughout bending of an articulating neck.

There are two general approaches used to minimize and eliminate RFI and EMI. And they both have shortcomings. The first approach is to filter noise or interference out of the desired signals transmitted in the elongated flexible neck. But this approach is expensive and complex. The second approach involves the use of shielded signal cables. But adding braid or shielding to a signal carrying cables can affect its flexibility and adds to the girth or diameter of to the cable. And both are important. Maximum flexibility is need for inspection. Furthermore, the constant bending may cause fatigue and wear of the braid—This can result in the loss of electrical continuity, resulting in loss of the shielding effect. The invasive nature of some inspections requires a minimum cross-section or girth.

So there is a need for an improved elongated bendable neck providing RFI shielding.

SUMMARY OF THE INVENTION

An object of the invention is an elongated flexible neck providing RFI shielding.

Another object of the invention is a flexible elongated neck construction giving improved flexure properties.

Yet another object of the invention is an improved elongated articulating neck that provides electrical continuity along the entire length of the neck.

In a broad sense, the above and other objects are attained by an elongated flexible neck with a series of individual electrically conducting parts that incorporate the use of self adjusting electrically conducting members. Such parts each have a passageway there through and are pivotally joined together with the passageways being aligned along the length of the neck. A self-adjusting electrically conducting member connects immediately adjacent individual parts in electric communication. And the self-adjusting members maintain electrical communication between the parts throughout movement of the parts during flexure. So the neck maintains electrical continuity along its length. The spacing between the pivotally joined parts is sized to be a barrier to predetermined radio frequencies.

In another sense, the objects are attained by an elongated articulating neck including a series of individual tubular parts that provides radio frequency shielding by keeping the individual tubular parts in electrical communication—thereby provide electrical continuity along the length of the neck. The tubular parts, which are capable of conducting electricity, have their openings aligned along the length of the elongated articulating neck to form a passage there through. A swivel tab is formed at one end the wall of the tubular parts; a counterpart swivel socket is formed at other end. Adjacent tubular parts are pivotally joined together by inter-engagement of the swivel tabs in the swivel sockets with the each swivel tab pivoting around a pivot axis. The swivel tabs have a recess formed therein with its opening positioned at the forward portion thereof. The edge surface defining the recess including a rear portion facing the opening of the recess along which is located the pivot axis of the swivel tabs. A biasing member extends from the wall into the swivel sockets. And such member terminates in engagement with the edge surface at the pivot axis of the swivel tab. The biasing member exerts sufficient force against such edge surface to maintain electrical contact therewith throughout flexure of the elongated neck. The spacing between the pivotally joined parts being sized to be a barrier to predetermined radio frequencies.

Another aspect of the invention provides an elongated articulating inspection neck having various bending radii. Such a neck includes a series of individual parts having an opening there though. The opening of the parts are aligned along the length of the articulating neck to form a passageway through the neck. Such parts are formed with a pair of opposed swivel tabs at one side and are formed with a pair of diametrically of counterparts swivel sockets at the opposite side. Accordingly, along the length of the neck the adjacent parts are pivotally joined together by inter-engagement of the swivel tabs in the swivel sockets. The wall of such parts is formed with a pair of diametrically opposed finger tabs located between the pair of swivel tabs that are on one side and with a pair of counterpart finger sockets located between the pair of swivel sockets at the opposite side. Finger tabs are moved into finger sockets during bending of the neck and are stopped by the bottom thereof to limit bending radius of the neck. And the finger tabs and the finger sockets are dimensioned to provide different a bending radius on opposite sides of the neck. And in some certain instances dimensions of the finger tabs and finger sockets vary along the length of the neck.

Advantages from the use of the instant invention are important. First, electrical continuity along the length of the flexible neck provides is an RFI shield that contains radio frequency emissions present within the neck and shields radio frequency emissions outside the neck from entering the interior of the neck. And the invention allows both engineering of bending radii and the amount of articulation of flexure.

Other objects and advantages will become more apparent as the invention is described in more detail with reference made to the as accompanying drawings.

DESCRIPTION OF THE DRAWINGS

FIG. 1 illustrates the neck joined at one end to an inspection head or sensor used in invasive medical procedures.

FIG. 2 illustrates only one of the four control cables depicted in FIG. 1 so that the guide grooves in the exterior surface of inner links of the neck can be more clearly seen.

DESCRIPTION OF THE PREFERRED EMBODIMENTS

An elongated flexible neck according to the invention has wide application in the inspection field. But it has particular applicability in situations where such things such as RFI shielding and engineered flexibility are important operational needs. In this regard, an elongated flexible neck embodying the principles of the invention is especially applicable in the medical field where electronic inspection devices are subject to RFI. For example, the invention is well suited for use in such devices as endoscopes, orthoscopes, ultrasound transducer probes, and other invasive imaging and therapeutic medical devices where the device is inserted in a patient's body. Besides use in the medical field, the invention has use in such applications as inspection of internal combustion motors, jet engines, and other inspection applications.

Figure 1:
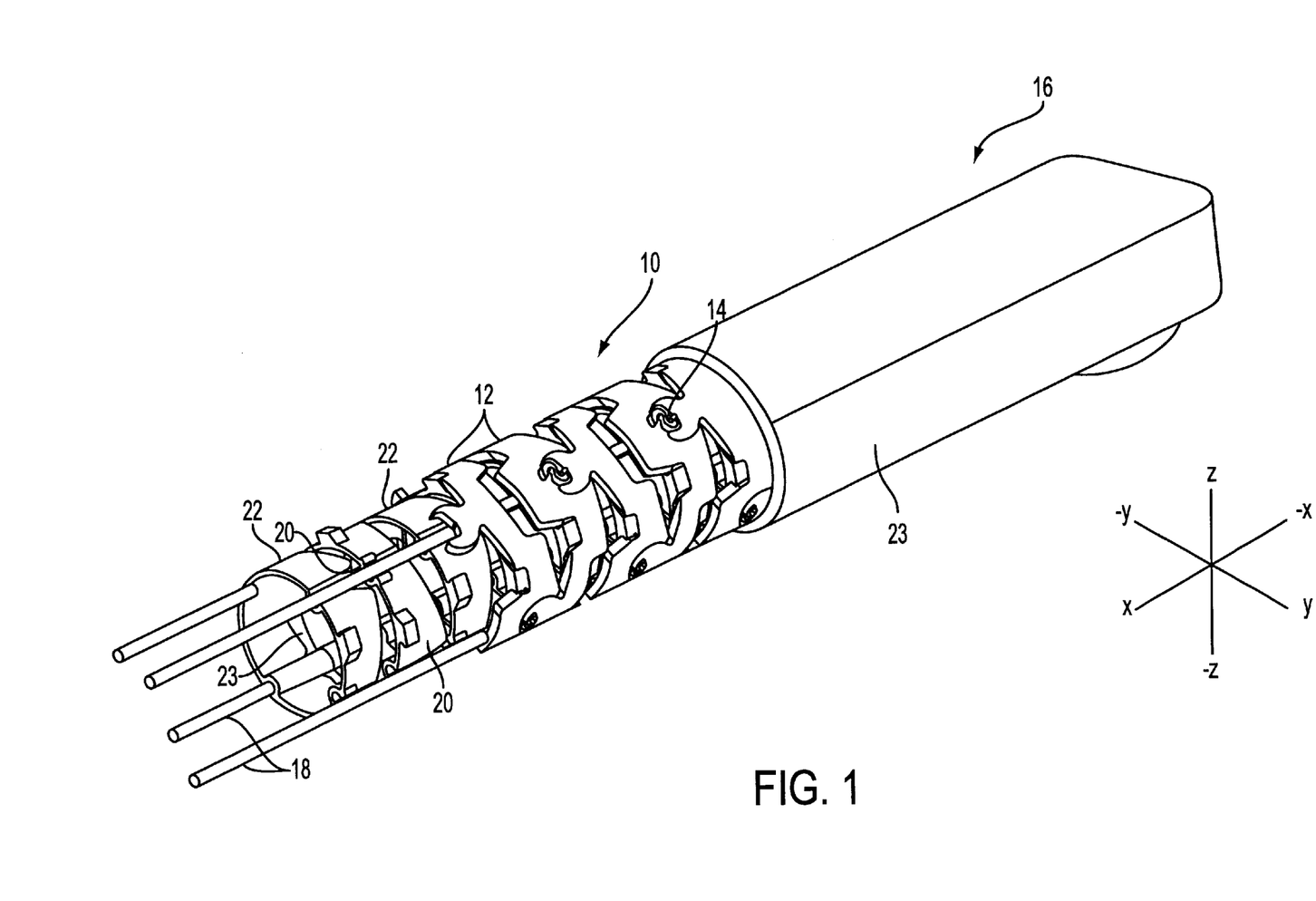
FIG. 1 is a partly cut away perspective view of a portion of a dual axis elongated articulating neck according to the principles of the present invention.
Figure 2:
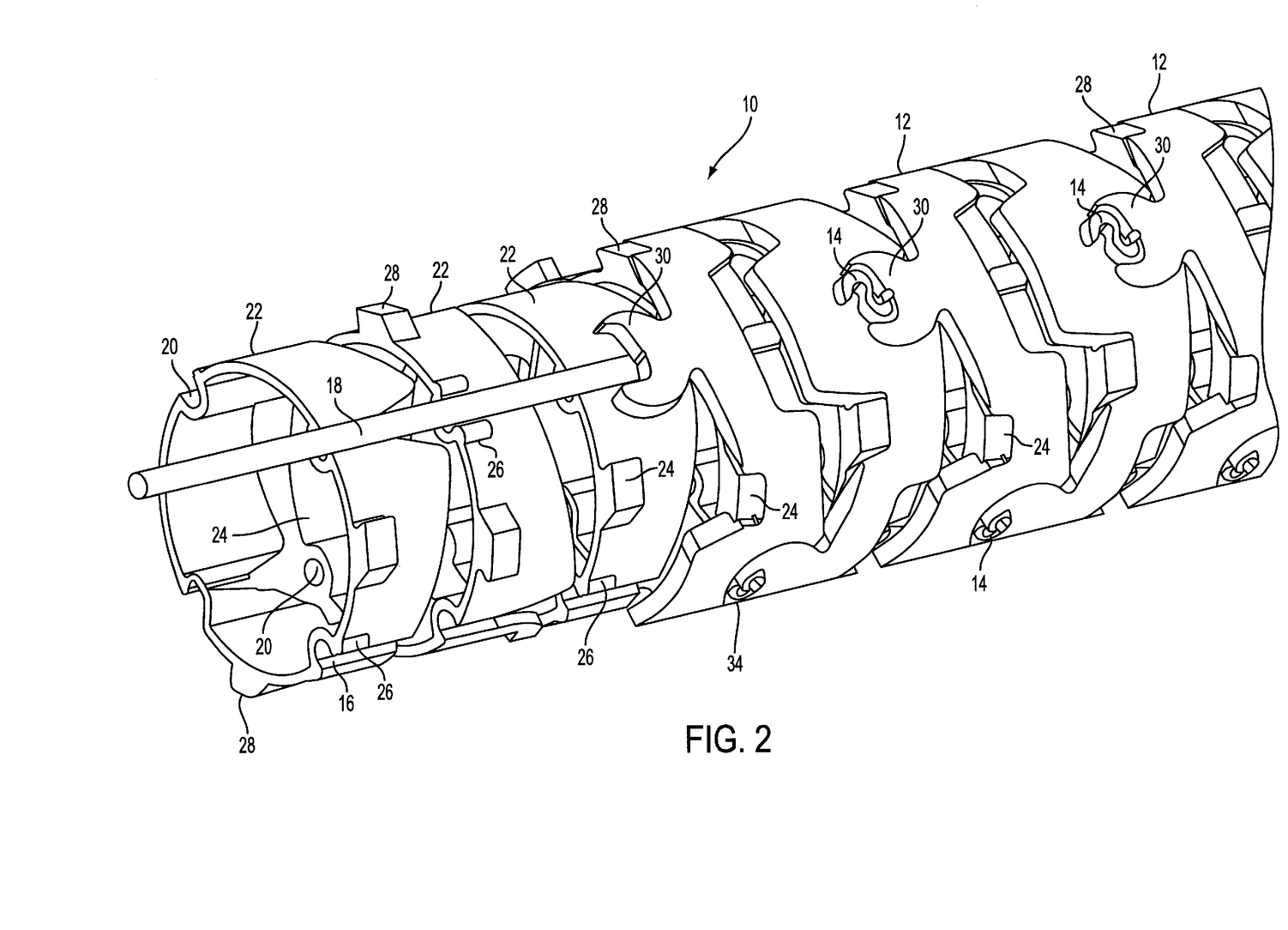
FIG. 2 is an enlarged perspective view of a portion of the elongated articulating neck shown in FIG. 1.

FIGS. 1 and 2 illustrate an embodiment of a dual axis flexible neck 10 according to the principles of the invention. The neck 10 includes independent individual electrically conductive parts having a passageway there though, shown as tube-like parts or sleeves 12. The parts 12 are pivotally joined together with the passageways of each of the parts 12 aligned along the length of neck 10.

Self-adjusting electrically conducting members 14 connect immediately adjacent individual parts 12 in electrical communication.

And these self-adjusting members 14 maintain electrical communication between the parts 12 throughout movement of the parts 12 during flexure of the neck 10. Consequently, the members 14 provide continuous electrical communication between the parts 12 along the length of the neck 10. As shown in FIGS. 1 and 2 the self-adjusting members 14 are electrically conducting compression springs having a serpentine shape. The members 14 are located on the end parts 12 and integral therewith. The spring members 14 urge themselves against at the pivot point of adjacent pivotally joined parts 12, as more fully explained hereafter.

The parts or sleeves 12 are made of electrically conductive material, such as metal, metal covered plastic or conductive plastic. As shown, the parts 12 are made of tubular stainless steel that has an outside diameter of 0.320 inches and has a wall thickness of 0.018 inches.

As shown in FIG. 1 one end of the neck 10 is joined to an inspection head assembly 16.

Control of the neck 10 is gained, in the embodiment of FIGS. 1 and 2, by four control cables 18. In this case the control cables 18 are spaced equally apart around the circumference of the neck 10 ninety degrees (90°)from each other. The control cables 18 extend through guide passageways or grooves 20 on the exterior surface of individual inner ring member or links 22. At the other end on the neck 10, the cables 18 join to a steering wheel or other type of conventional steering mechanism (not shown). In operation, movement, such as shorting or pulling, of the cables 18 in the grooves 20 through use of a steering device flexes or bends the neck 10 in desired amounts and in directions to control the position of the head assembly 16.

The grooves 20 have a diverging section 21 to allow for cable flexure.

A conventional exterior protective sheathing tube 23 covers the elongated neck 10. As shown, the tube 23 is made of a conventional elastomer.

An internal conduit 24 extends its entire length of the neck 10 accommodates interconnections, such as fiber optic cables, drive shafts, electrical conductors, hydraulic or pneumatic lines, and system electronics needed by the particular head assembly 16. When the head assembly 16 is, for example, an ultrasound transducer, the conduit 24 accommodates flexible electronic interconnections that join to the ultrasound transducer.

Each of the sleeves 12 encircles an inner link 22 in snug fit relation to form a composite independent part.

Figure 3:
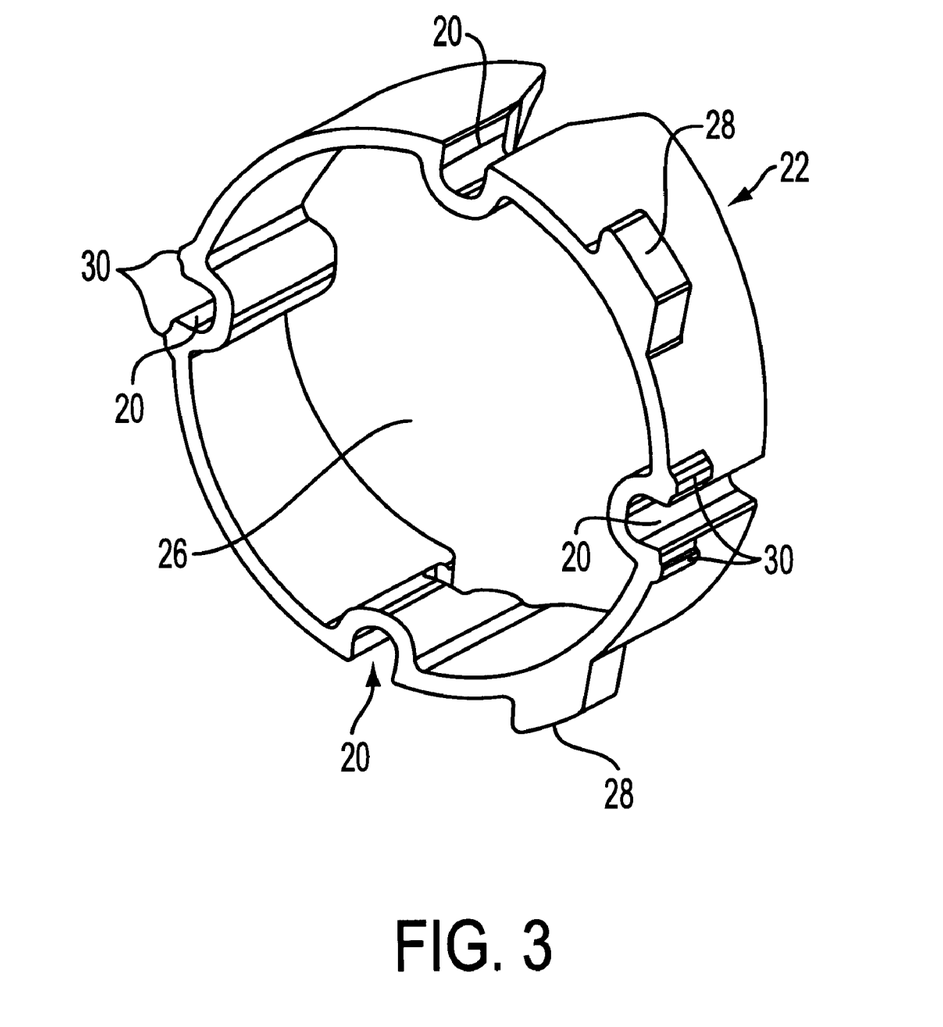
FIG. 3 is a perspective view of one of the inner links used to construct the elongated articulating neck shown in FIGS. 1 and 2.

FIG. 3 is an enlarged perspective view of an inner link 22. As shown, the link 22 includes a passageway or lumen 26 and external surface guide grooves 20, which (as indicated) are spaced 90 degrees apart around the circumference of the link 22. Further, on the exterior surface of the link 22 are two spaced alignment tabs 28 located on one side of the link 22. The tabs 28 are spaced on opposite sides of one of the grooves 20. On opposite sides of the link 22 are two pairs of raised portions or bumps 30, each pair is located immediately adjacent a groove 20. The tabs 28 are used to keep the link 22 from rotation movement on the associated sleeve 12; the bumps 30, to hold the links 22 in snug or press fit relation with the associated sleeve 12. Each lumen 26 of links 22 combine to form the conduit 24 of the neck 10.

In FIGS. 1 and 2, the links 22 are made of an aluminum/bronze alloy, but they can be made of other material, such as plastic and metal coated plastic. The link 22 does not need to be made of an electrically conductive material.

Figure 4:
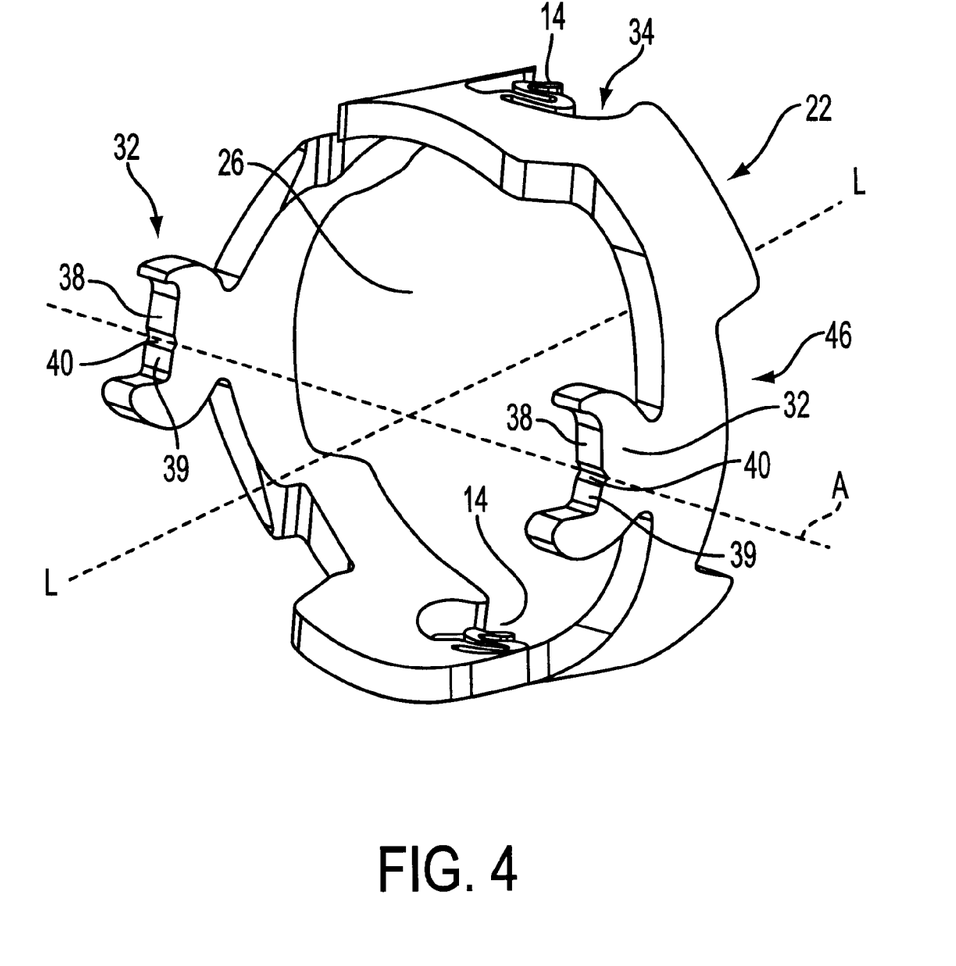
FIG. 4 is a perspective view of one of the outer sleeve or part used in the construction of the elongated articulating neck shown in FIG. 1. The longitudinal axis of such neck is shown in dashed lines denoted by L—L.
Figure 5:
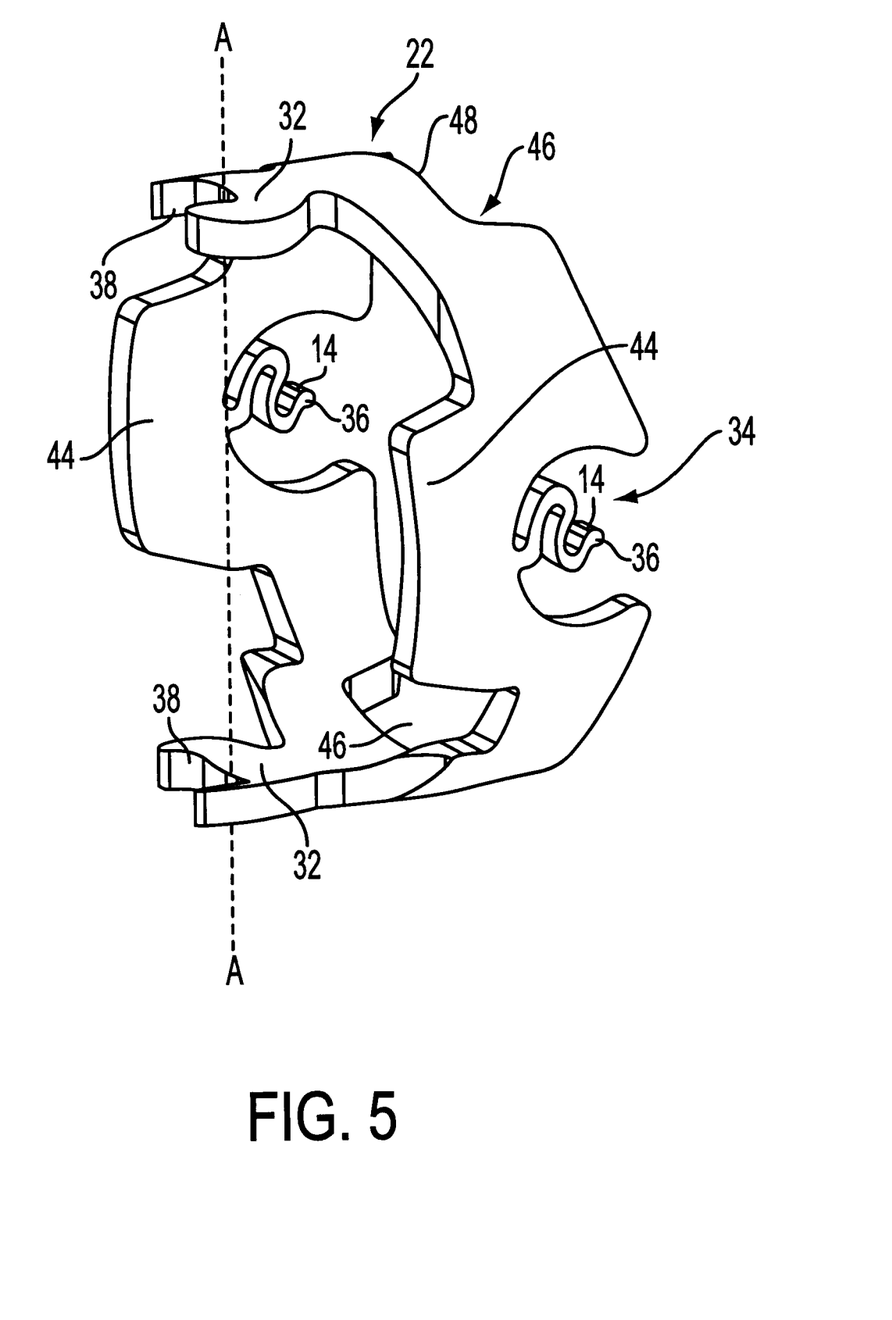
FIG. 5 is another perspective view of the outer sleeve or part illustrated in 4, but rotated 90 degrees with respect to the sleeve illustrated in FIG. 4. This is done to show more clearly the swivel joints or tabs and swivels sockets of the part.
Figure 6:
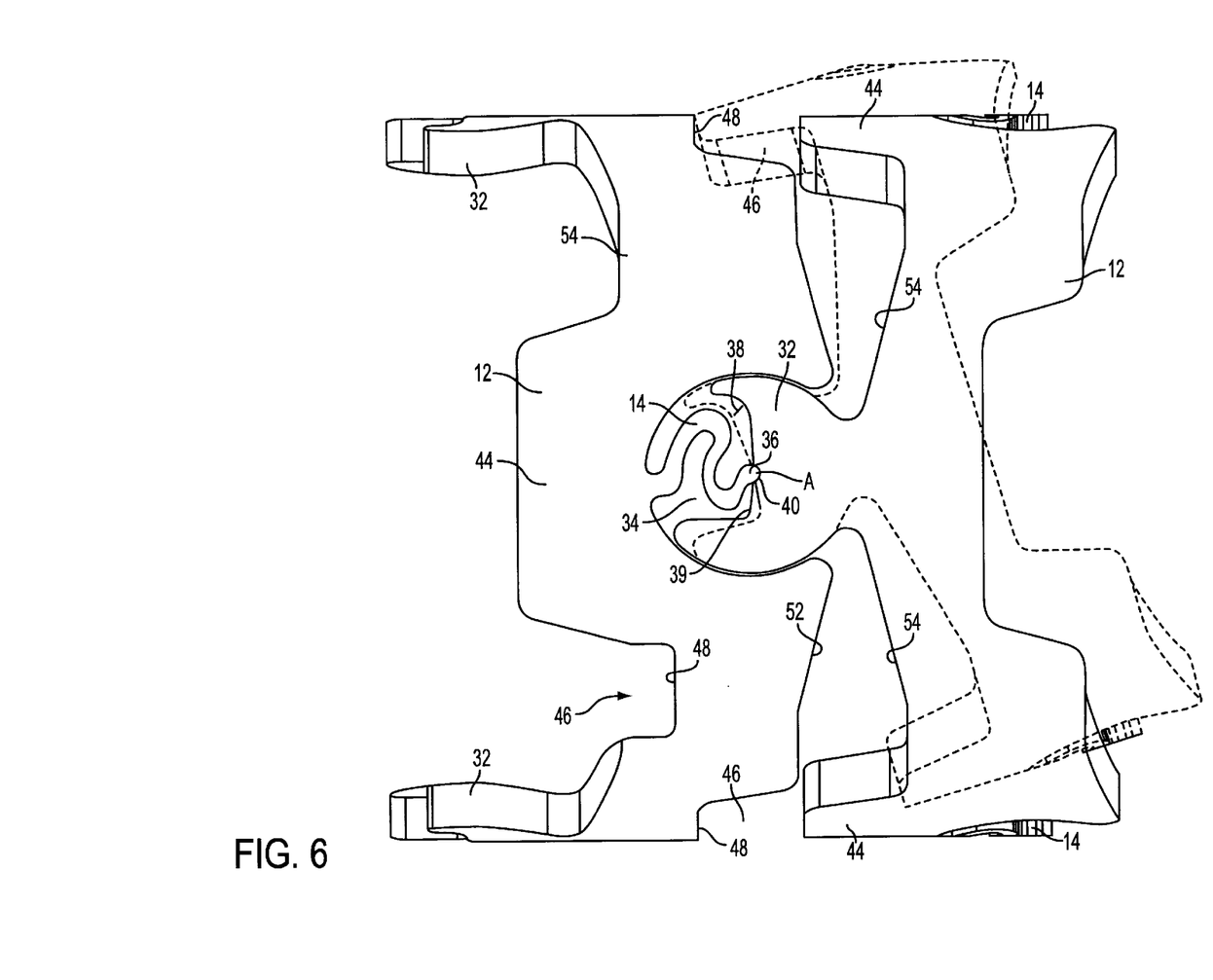
FIG. 6 is a side elevation view of a pair of joined together sleeves. The swivel tabs of one of the sleeves are enter-engaged with the swivel sockets of the other sleeve. The reference letter A identifies the pivot axis of the swivel tabs. The pivot axis A is also shown by dashed lines in FIGS. 4 and 5.

Referring to FIGS. 4, 5, and 6, it can be more clearly seen how the sleeve parts 12 of the neck 10 are pivotally joined together. Each of the parts 12 is formed with a pair of diametrically opposed swivel joints or tabs 32; the other end of the sleeve 12 is formed with a pair of diametrically opposed counterpart swivel sockets 34. The swivel sockets 34 and the swivel tabs 32 are on opposite ends of the sleeve 12 and located circumferentially 90 degrees from each other. The shape of the tabs 32 is circular and sockets 34 are also circular in shape. The tabs 32 is and the sockets 34 have essentially the same diameter. So when tabs 32 of one part 12 are fitted or inter-engaged in sockets 34 of another part 12, the tabs 32 are pivotally moveable in the sockets 34 around a pivot axis A (see FIGS. 4 and 6).

As shown in FIGS. 1–6, the diameter of the tabs 32 is 0.090 inches and the diameter of the sockets 34 is 0.092 inches.

The neck 10 is shown to be a dual-axis flexible neck. The swivel tabs 32 and counterpart swivel sockets 34 of immediately adjacent parts 12 alternate in rotational offset of 90 degrees about the X axis, or lengthwise axis of the neck 10. Consequently, the neck 10 can bend in the +Y and −Y directions and the +Z and −Z direction (see FIG. 1). As a result, the neck 10 can be articulating in any direction within the Y-Z plane.

Figure 7:
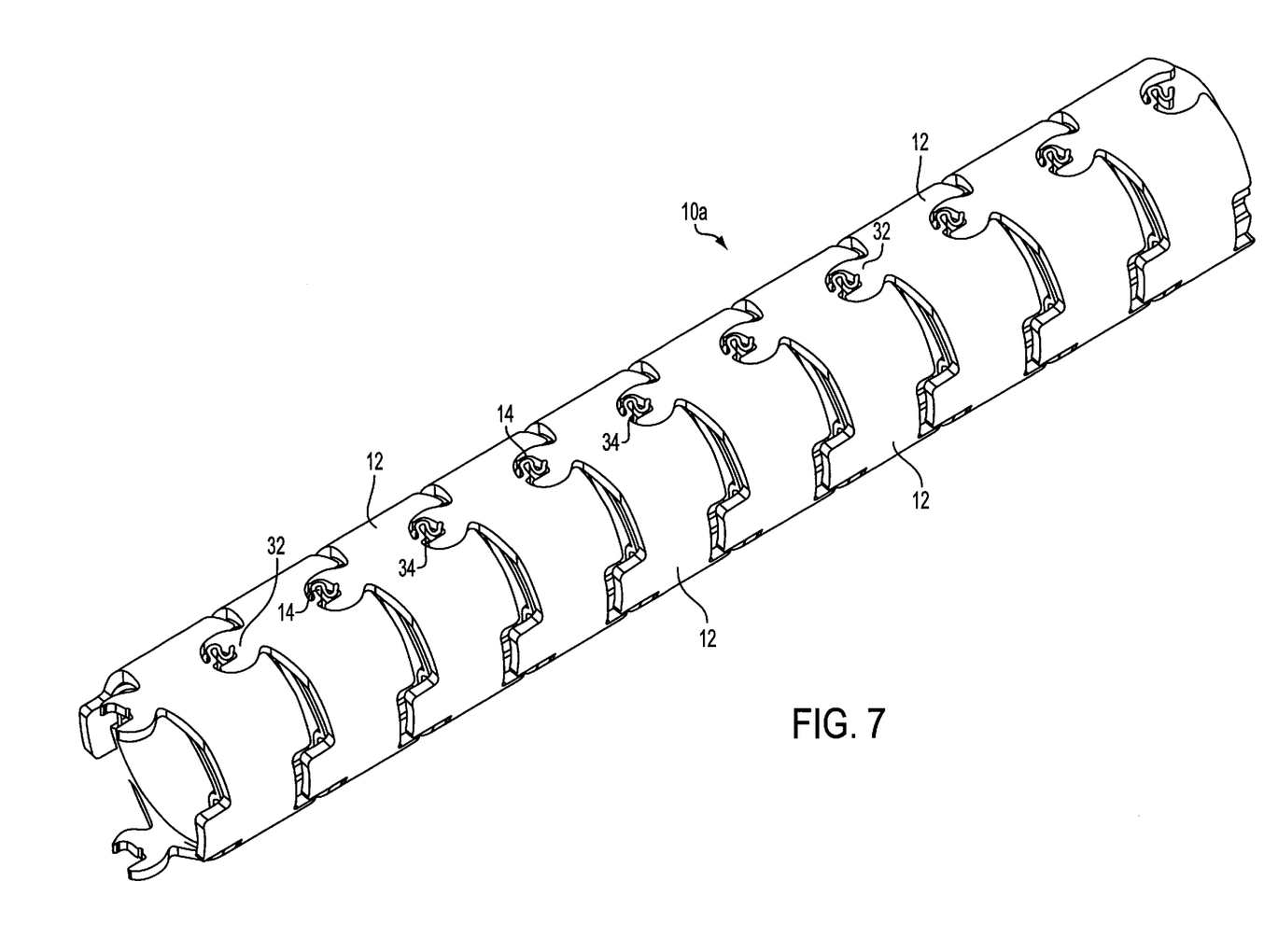
FIG. 7 is a perspective view of a single axis elongated articulating neck according to the principles of the invention.

An articulating neck 10a with a single axis has the swivel tabs 32 of parts 12 and the corresponding swivel sockets 34 of parts 12 in alignment as shown in FIG. 7. A single axis is explained in U.S. Pat. No. 5,749,828, which is incorporated herein.

An electrically conducting spring connector or member 14 extends from the wall of the part 12 into each of the swivel sockets 34. The spring member 14 has a serpentine shape and includes a rounded end 36.

The forward portion of each of the swivel tabs 32 is shaped with a recess 38 opening at the tab's forward portion. And the edge surface 39 defining the recess 38 extends to include a rear section or portion facing toward the opening. Along the edge surface 39 that defines the recess 38 formed therein a notch 40 (facing the open of the recess 38). The rounded end 36 of the serpentine spring 14 engages immediately adjacent parts 12 at the notch 40. The pivot axis A for the tabs 32 in sockets 34 passes through the center of notch 40 and the center of the rounded end 36 of the spring 14.

FIG. 6 shows one side of two adjacent parts 12 pivotally joined together. A swivel tab 32 is shown seated in place to move pivotally around pivot axis A in a swivel socket 34. As can be seen, the rounded end 36 of the spring connector 14 is seated in the channel 40.

The serpentine spring connector 14 is designed to press with sufficient force against the surface 39 at the channel 40 that electrical contact is maintained throughout bending or flexing of the neck 10. In the embodiment shown the spring contact 14 pushes against the surface 39 at the channel 40 with a one pound force and with a travel of 0.0022 inches.

Figure 8:
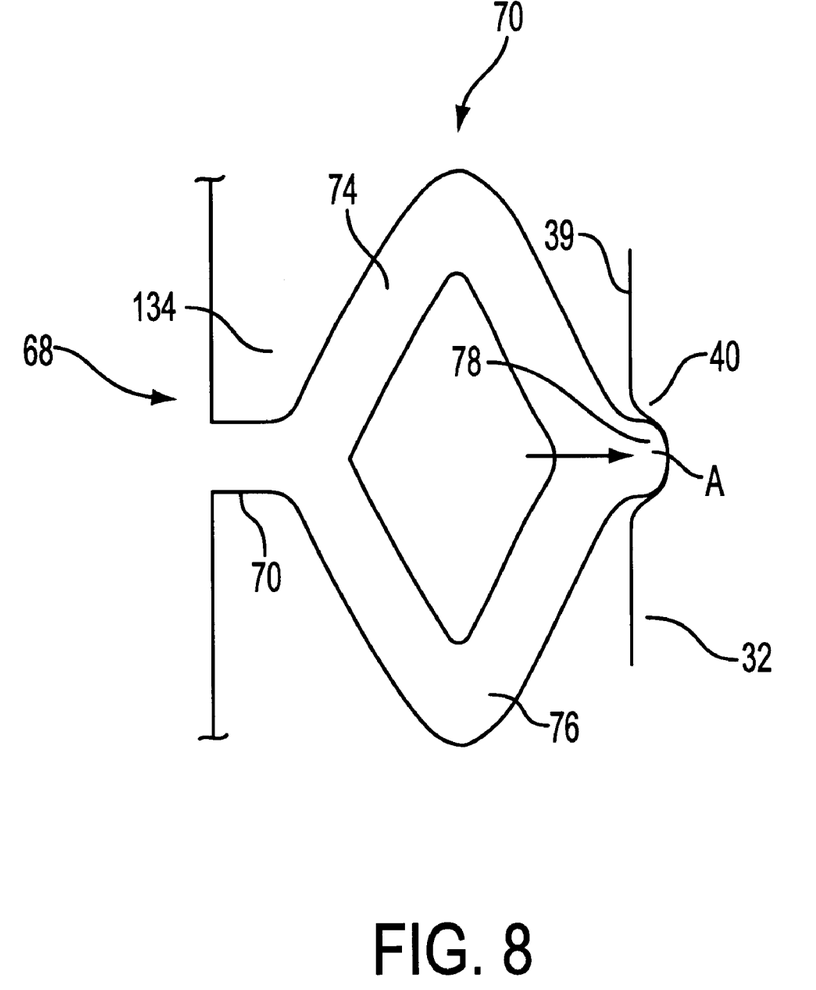
FIG. 8 illustrates an enlarged view of an alternate compression type self-adjusting member according to the principles of the invention.

FIG. 8 shows alternate embodiment of the invention using a different self-adjusting member connecting individual parts in electrical communication. As shown, a spring 70 extends from a wall of an individual part 68 (like the part 12, except for the spring 70) in the swivel socket 34 to press against an edge surface 39 defining a recess 38 of a swivel tab 32. As shown, the spring 70 includes a base 72, a curved portion 74, a curved portion 76, and an end 78. The base 72 bifurcates into the curved portions 74 and 76. These curved portions come together and form the end 78. Like the embodiment of the FIGS. 1 and 2, the end 78 of the spring 70 is rounded and engages the channel or notch 40, which is at the center of rotation of swivel tabs 32.

The end of the end 78 the spring 70 is urged with sufficient against the surface defining the notch 40 to maintain electrical communication between parts 68 throughout movement of the parts during flexure of the elongated flexible neck 10.

Figure 9:
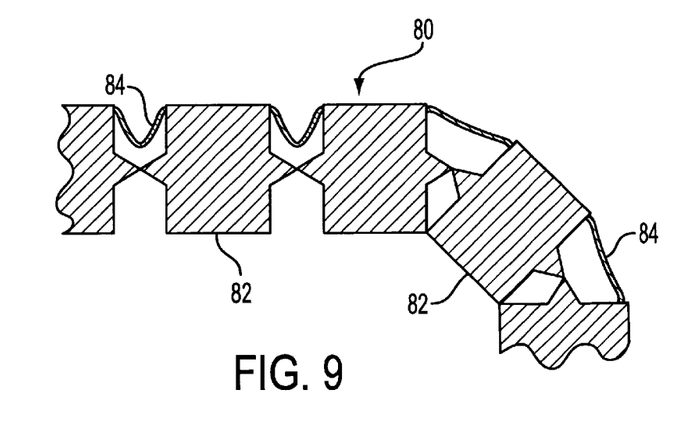
FIG. 9 illustrates an alternate embodiment of an elongated flexible neck according to the principles using a self-adjusting member in the form connecting conducting tether with catenary.
Figure 10:
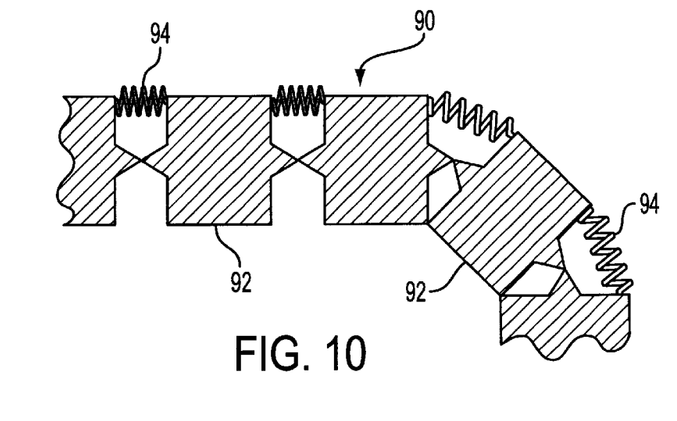
FIG. 10 illustrates another alternate embodiment of an elongated flexible neck according to the principles using a self-adjusting member in the form of a conducting tension or extension spring.

Other embodiments of an articulating neck according to the invention may use other type of self-adjusting member to maintain electrical continuity along the length a flexible neck. Some resilient members can employ different magnitudes of biasing forces and travel. In some instances, some embodiments may use an electrical self-adjusting connector that does not employ a biasing force. For example, one such articulating neck 80 uses flexible electrical connectors or wires 84 that connect adjacent pivotally connected parts 82. The wires 84 employ catenary as generally illustrated in FIG. 9. The catenary of the flexible members 84 changes as it straightens out during bending of the neck 80. And in other instances, an articulating neck according to the invention might use a self-adjusting member in the form of a tension or compression spring. FIG. 10 one such embodiment where a flexible neck 90 uses tension or compression springs 94 that connect adjacent pivotally connected parts 92. The springs 94 stretch or compress during bending of the neck 90. The self-adjusting members must maintain electrical communication between the adjacent parts during bending of the elongated flexible neck.

The bending radius of the neck 10 is controlled in both the Y and Z directions by interaction of finger joints 44 and finger sockets 46 on the ends of the parts or sleeves 12. FIG. 6 indicates in dashed lines what happens to the finger joints 44 and the finger sockets 46 on bending binding neck 10. The finger joint 44 on the short side of the neck 10 (indicated at the top of FIG. 6) advances in the associated finger socket 46 and is stopped by the bottom stop wall 48 of the socket 46. The finger joint 44 on the long or opposite side of the neck 10 (indicated at the bottom FIG. 6) retreats in the associated finger sockets 46. The below make the desired bending motion. In this embodiment, the finger joints 44 are same lengths and the finger sockets 46 are the same depths.

The space between the pivotally joined parts 12 is sized to be a barrier to predetermined radio frequencies. In this regard, it is known that the longest dimension of an opening or space determines the radio frequencies shielding effect. If the longest dimension of a space is less than $\lambda/4$ (where $\lambda = c/f$, and c is the speed of light and f is the frequency to be shielded by the space), the space will shield against frequencies f and below. The longest dimension of the space between the pivotally joined parts is the dimension between pivot points. It is noted that the speed of light is 299,792,458 meters per sec.

Articulating necks according to the principles can use various spacing according the frequencies, f, to be shielded.

Again, as shown in FIGS. 1–6 the neck 10 is a dual axis. As indicated, the swivel tabs 32 and the corresponding sockets 34 of each immediately adjacent are rotationally offset 90 degrees about the X-axis or lengthwise of axis of the neck 10. So different alternating parts 12 are involved in bending in the Y-axis and in the Z-axis. As shown in FIGS. 1, 2, 4, 5, and 6, the bending radius is the same in both the Y-axis and Z-axis.

Figure 11:
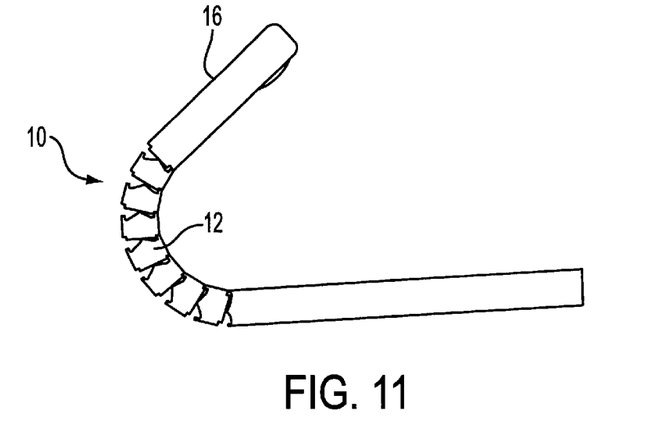
FIG. 11 depicts bending of the elongated flexible neck shown in FIGS. 1–6.

FIG. 11 illustrates the bending radius of the neck 10. The bending radii are equal in the X and Y-axes.

The bend radius or bend articulation can be varied or engineered by changing the length or diameter of parts 12 and the part to part gap between parts 12.

Figure 12A:
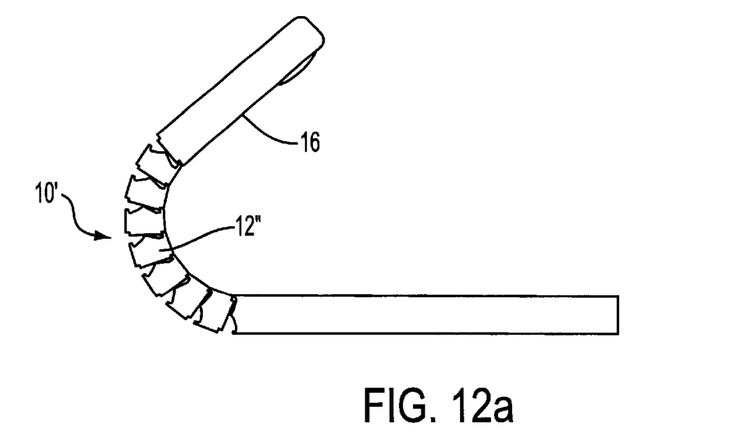
FIGS. 12a and 12b are depictions of an elongated flexible neck according to the principles of the invention having different bending radii.
Figure 12B:
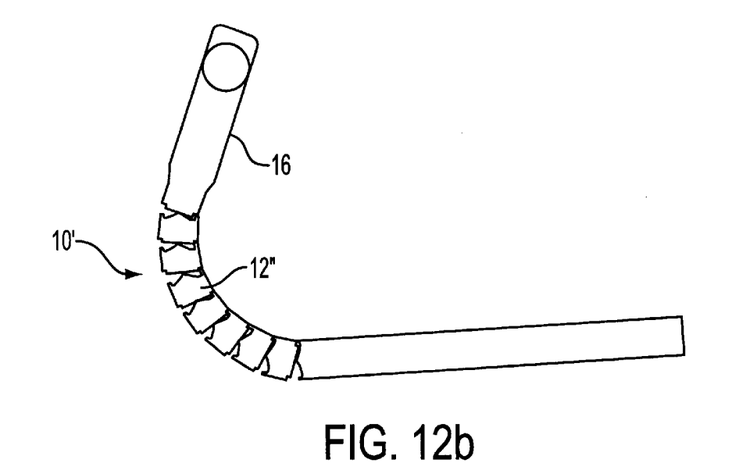

In one such embodiment, shown in FIGS. 12a and 12b, an elongated neck 10' is made of identical parts 12'. But unlike parts 12, finger joints 44 are of different lengths and the finger sockets 46 are of different depths. So the bending radii in the X and Y-axes are different. FIG. 12a shows the bending radius in the Z-axis; FIG. 12b, in the X-axis.

Figure 13A:
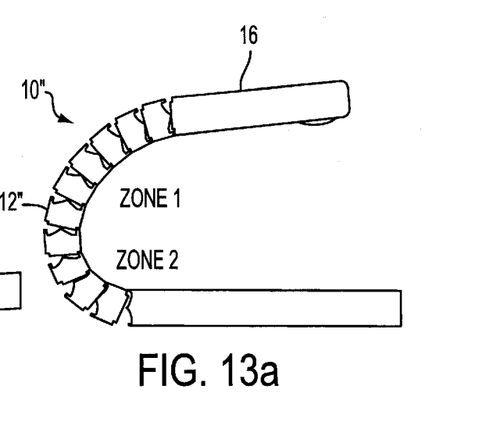
FIGS. 13a and 13b are depictions of an elongated articulating neck according to the principles of the invention that is constructed to have various engineered bending radii along its length.
Figure 13B:
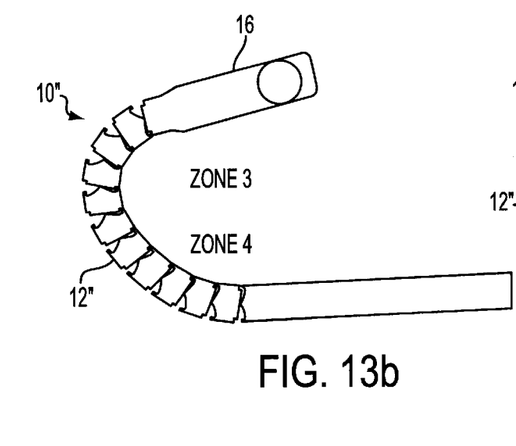

FIGS. 13a and 13b illustrate another embodiment of a flexible neck according to the principles of the invention. An elongated flexible neck 10" is shown that is made of parts 12". In the neck 10 the are parts 12 are identical, but in the neck 10" the parts 12" are not identical. The lengths of the finger joints 44 and the depths of the finger sockets 46 of the parts 12" are mixed along the length of an elongated neck 10" according to engineered bending characteristics desired. In other words, the neck 10" is given different bending properties along its length both in the Y and Z-axes. In FIG. 13a, the neck 10" in the Y-axis the bending characteristics along its length are different in zone 1 than zone 2. In FIG. 13b, the neck 10" in the Z-axis the bending characteristics along its length are different yet in the zones 3 and 4.

Figure 14:
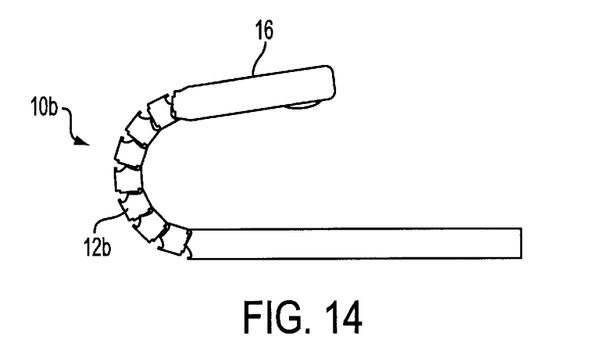
FIG. 14 depicts a flexible neck according to the principles of the invention that has a smaller bend radius.

FIG. 14 shows a flexible neck 10b where parts 12b have a smaller diameter than parts 12 of the flexible neck 10, but in all other respects are identical. Consequently, the bend radius or neck 10b is smaller than the bend radius of neck 10. The gap or space between the parts 12b of the neck 10b is the same as the gap or space between the parts 12 of the neck 10.

Figure 15:
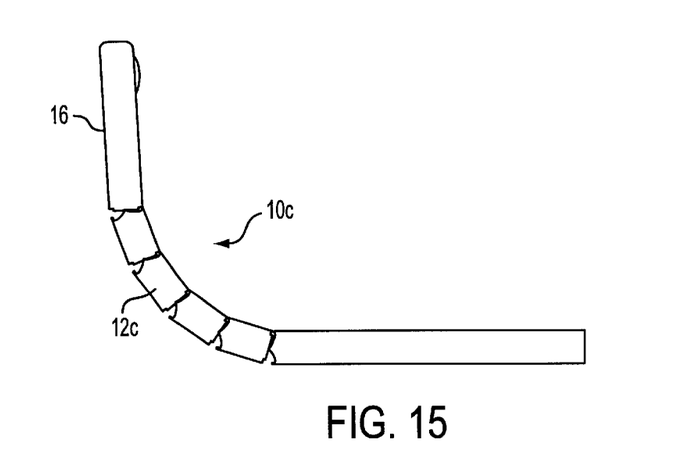
FIG. 15 depicts a flexible neck according to the principles of the invention that has a larger bend radius.

FIG. 15 shows another embodiment of a flexible neck according to the invention. A neck 10c is illustrated where parts 12c are longer than parts 12 of the neck 10. Also, the number of parts 12c of flexible 10c is less than the number of parts 12 of flexible neck 10. Consequently, the bend radius of the neck 10c is larger than the bend radius of the neck 10. The gap or space between 12c of neck 10c is the same as the gap or space between the parts 12 of the neck 10.

These embodiments of the elongated flexible neck according to the principles of the invention can be constructed using single, dual, or more axes. In same instances, it may be advantages to use parts of other shapes that are not circular in cross section. For example, it might be useful in some instances to construct a flexible neck in accordance with the invention that use parts, for example, having an oval, square, or rectangular in cross section.

It is apparent from the foregoing that, within the scope of the invention, modifications and different embodiments may be made other than as herein disclosed. The present disclosure is merely illustrative, the invention comprehending all variations thereof.

We claim:

1. An elongated flexible neck providing radio frequency shielding comprising:
   a series of individual electrically conducting parts each having a passageway there through, such individual parts being pivotally joined together with the passageways being aligned along the length of the neck; and
   a self-adjusting electrically conducting member connecting immediately adjacent individual parts in electrical communication, such member maintaining electrical communication between such parts throughout movement of the parts during flexure of the neck thereby maintaining electrical continuity along the length of the neck, the spacing along the length of the neck between the pivotally joined parts being sized to be a barrier to predetermined radio frequencies.

2. The elongated neck of claim 1, wherein the electrically conducting member is flexible.

3. The elongated neck of claim 2, wherein the electrically conducting member is a metal.

4. The elongated neck of claim 1, wherein the electrically conducting member is a spring.

5. The elongated neck of claim 4, wherein the spring is a compression spring.

6. The elongated neck of claim 5, wherein the spring extends from one of each pair of pivotally joined parts to terminate at an end being urged against the other part of the pair at the location of the pivot axis of the pair.

7. The elongated neck of claim 6, wherein the spring is serpentine in shape.

8. The elongated neck of claim 7, wherein the end of the serpentine shaped spring is rounded.

9. The elongated neck of claim 6, wherein the spring includes a base, a pair of curved portions bifurcating at the base, and an end formed by the joining together of the curved portions.

10. An elongated flexible neck providing radio frequency shielding comprising:
    a series of individual electrically conducting parts each having a passageway there through, such individual parts being pivotally joined together with the passageways aligned along the length of the neck; and an electrically conducting spring, the spring extending from one of each pair of pivotally joined parts to terminate at a end being urged against the other part of the pair at the location of the pivot axis of the pair, such spring maintaining electrical communication between such parts throughout movement of the parts during flexure of the neck thereby maintaining electrical continuity along the length of the neck, the spacing between the pivotally joined parts being sized to be a barrier to predetermined radio frequencies.

11. An elongated articulating neck providing radio frequency shielding comprising:

a series of individual tubular parts capable of conducting electricity, the opening through such tubular parts aligned along the length of the elongated articulating neck to form a passage there through, the wall of such parts being formed with a swivel tab at one end and being formed with a complementarily sized swivel socket at other end, adjacent tubular members being pivotally joined together by inter-engagement of the swivel tabs in the swivel socket with the each swivel tab pivoting around a pivot axis, the swivel tab having a recess formed therein with its opening positioned at the forward portion thereof, the edge surface defining the recess including a rear portion facing the opening of the recess along which is located the pivot axis of the swivel tab; and a member extending from each of the walls into the swivel socket, such member terminating in engagement with the edge surface at the pivot axis of the swivel tab, the member exerting sufficient force against such edge surface to maintain electrical contact therewith throughout flexure of the elongated neck, the spacing between the pivotally joined parts being sized to be a barrier to predetermined radio frequencies.

12. The elongated flexible neck of claim 11, wherein the member is integral with the wall.

13. An inspection device comprising:

an elongated flexible neck providing radio frequency shielding including a series of individual electrically conducting parts each having a passageway there through, such individual parts being pivotally joined together with the passageways aligned along the length of the neck;

an electrically conducting spring, the spring extending from one of each pair of pivotally joined parts to terminate at a end being urged against the other part of the pair at the location of the pivot axis of the pair, such spring maintaining electrical communication between such parts throughout movement of the parts during flexure of the neck thereby maintaining electrical continuity along the length of the neck; and an inspection sensor joined at one end of the elongated flexible neck, the spacing between the pivotally joined parts being sized to be a barrier to predetermined radio frequencies.

14. An inspection device comprising:

an elongated articulating neck including a series of individual tubular parts capable of conducting electricity, the opening through such tubular parts aligned along the length of the elongated articulating neck to form a passage there through, the wall of such members being formed with a swivel tab at one end and being formed with a complementarily sized swivel socket at other end, adjacent tubular members being pivotally joined together by inter-engagement of the swivel tabs in the swivel socket with the each swivel tab pivoting around a pivot axis, the swivel tab having a recess formed therein with its opening positioned at the forward portion thereof, the edge surface defining the recess including a rear portion facing the opening of the recess along which is located the pivot axis of the swivel tab, a biasing member extending from the wall into the swivel socket, such member terminating in engagement with the edge surface at the pivot axis of the swivel tab, the biasing member exerting sufficient force against such edge surface to maintain electrical contact therewith throughout flexure of the elongated neck, the spacing between the pivotally joined parts being sized be a barrier to predetermined radio frequencies; and an inspection sensor connected to one end of the neck.

15. An elongated articulating neck for providing radio frequency shielding and controlling the position of a head connected at one end thereof comprising:

individual tubular links positioned in an end-to-end relationship along the length of the elongated articulating neck, the exterior surface of each of such links being formed with spaced-apart grooves extending axially of its tubular link, the grooves of each of the tubular links being aligned with each other to form together a guide passageway extending the length of the elongated neck;

control cables extending through the grooves, such cables being connected at the same ends to the head; and individual tubular sleeves capable of conducting electricity encircling individual tubular links in snug-fit relationship and covering the grooves of the individual links, such tubular sleeves positioned in an end-to-end pivotally joined together relationship along the length of the elongated articulating neck, each of such sleeves having their wall formed with a swivel tab at one end and having its wall at the opposite end formed with a counterpart swivel socket, the tubular members being joined together with the swivel tab of each of the tubular members inter-engaged with the swivel socket of an immediately adjacent tubular member with pivotal movement of the swivel tab therein, the swivel tab having a recess formed therein with its opening positioned at the forward portion thereof, the edge surface defining the recess including a rear portion facing towards the opening of the recess and along which is located the center of rotation of the swivel tab in its swivel socket, the swivel socket including a biasing member extending to engage the rear portion of the edge surface at the center of rotation of the swivel tab, the biasing member exerting sufficient force against the edge surface at the center of rotation to maintain electrical contact therewith throughout pivotal movement of the swivel tab in the swivel socket.

16. An elongated articulating neck for providing radio frequency shielding and controlling the position of a head connected at one end thereof comprising:

Individual tubular links positioned in end to end relationship along the length of the elongated articulating neck, the exterior surface of each of such links being formed with spaced apart grooves extending axially of its tubular link lengthwise of the neck, the grooves of each of the tubular links being aligned with each other to form together a guide passageway extending the length of the elongated neck;

control cables extending in the grooves, each of the control cables being joined at same end to the head; and individual tubular sleeves capable of conducting electricity encircling individual tubular links in slide fit relationship and covering the grooves of the individual links, such tubular sleeves positioned in end to end pivotally joined together relationship along the length of the elongated articulating neck, each of such sleeves having its wall formed with a pair of diametrically opposed swivel tabs at one end and having its wall at the opposite end formed with a counterpart pair of diametrically opposed swivel sockets, the swivel sockets each being circumferentially offset midway between the swivel tabs on opposite sides of the tubular sleeve, the tubular sleeves being joined together with each of the pair of swivel tabs of each of the tubular sleeves inter-engaged with one of the pair of swivel sockets of an immediately adjacent tubular member with pivotal movement of the swivel tabs therein, each of the swivel tabs having a recess formed therein with its opening positioned at the forward portion thereof, the edge surface defining the recess including a rear portion facing towards the opening of the recess and along which is located the pivot point of the swivel tab inter-engaged in its swivel socket, each of the swivel sockets including a biasing member extending to engage the rear portion of the edge surface at the pivot point, each the biasing members each exerting sufficient force against its respective edge surface at the pivot point to maintain electrical contact with such edge surface throughout pivotal movement of the swivel tabs in their respective swivel sockets.

17. An elongated articulating neck comprising:

a series of individual parts having an opening there through, the opening through such parts aligned along the length of the articulating neck to form a passageway though the neck, such parts being formed with a pair of diametrically opposed swivel tabs at one side and being formed with a pair of counterpart swivel sockets at the opposite side, adjacent parts being pivotally joined together by inter-engagement of the swivel tabs in the swivel socket with each swivel tab pivoting around a pivot point, the individual parts also being formed with a pair of diametrically opposed finger tabs located between the pair of swivel tabs at the one side and with a pair of counterpart finger sockets located between the pair of swivel sockets at the opposite side, finger tabs being moved into the finger sockets during bending of the neck and stopped by the bottom of the finger sockets to limit the bending radius of the neck, the finger tabs and the finger sockets being so dimensioned to provide a different bending radius on opposite sides of the neck;

a self-adjusting electrically conducting member connecting immediately adjacent individual parts in electrical communication thereby maintaining electrical continuity along the length of the neck, the spacing along the length of the neck between the pivotally joined individual parts being sized to he a barrier to predetermine radio frequencies.

18. The elongated articulating neck of claim 17, wherein the finger tabs on one side of the neck are shorter than the other side of the neck.

19. An elongated articulating neck comprising:

a series of individual tubular parts, the opening through such tubular parts aligned along the length of the articulating neck to form a passageway there though, such pans being formed with a pair of diametrically opposed swivel tabs at one end and being formed with a pair of counterpart swivel sockets at the other end, the adjacent tubular parts being pivotally joined together by inter-engagement of the swivel tabs in the swivel socket with each swivel tab pivoting around a pivot point, the wall of such parts also being formed with a pair of diametrically opposed finger tabs located between the pair of swivel tabs at the same end thereof and with a pair of counterpart finger sockets located between the pair of swivel sockets at the other end thereof, finger tabs being moved into the finger sockets during bending of the neck and stopped by the bottom thereof to limit bending radius of the neck, the finger tabs and the finger sockets being so dimensioned to provide a different bending radius on opposite sides of the neck;

a self-adjusting electrically conducting member connecting immediately adjacent individual tubular pans in electrical communication thereby maintaining electrical continuity along the length of the neck, the spacing along the length of the neck between the pivotally joined individual tubular parts being sized to be a barrier to predetermined radio frequencies.

20. The elongated articulating neck of claim 19, wherein the finger tabs of the neck are of different lengths.

21. The elongated articulating neck of claim 20, wherein the finger tabs on one side of the neck is shorter than the other side.

22. The elongated articulating neck of claim 20, wherein the finger tabs vary along the length of the neck.

* * * * *